US00PP21480P2

(12) United States Plant Patent
Egger

(10) Patent No.: US PP21,480 P2
(45) Date of Patent: Nov. 16, 2010

(54) ***TRADESCANTIA* PLANT NAMED 'SUNSHINE CHARM'**

(50) Latin Name: ***Tradescantia* spp.**
Varietal Denomination: Sunshine Charm

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/460,335

(22) Filed: Jul. 17, 2009

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Kent L Bell
(74) *Attorney, Agent, or Firm*—Klarquist Sparkman, LLP

(57) ABSTRACT

A new and distinct form of *Tradescantia* plant characterized by yellow gold to yellow green foliage, lavender pink flowers, a compact clumping habit, and excellent vigor.

1 Drawing Sheet

Botanical denomination: *Tradescantia* spp.

Variety designation: 'Sunshine Charm'.

Parentage: *Tradescantia* Andersoniana Group 'Blue and Gold'×*Tradescantia* Andersoniana Group.

BACKGROUND OF THE INVENTION

The present invention relates to a new and distinct cultivar of *Tradescantia*, given the name, 'Sunshine Charm'. *Tradescantia* is in the family *Commelinaceae*. This new variety is from a planned breeding cross between *Tradescantia* Andersoniana Group 'Blue and Gold' (an unpatented plant) as the seed parent and *Tradescantia* Andersoniana Group (an unpatented plant) as the pollen parent. Compared to the seed parent, *Tradescantia* Andersoniana Group 'Blue and Gold', the new cultivar has lavender pink flowers rather than blue and a more compact habit. Compared to the pollen parent, *Tradescantia* Andersoniana Group, the new cultivar has yellow gold to yellow green foliage with single lavender pink flowers rather than double pink flowers and green foliage.

This plant exhibits the following characteristics that make it unique:

1. yellow gold to yellow green foliage,
2. lavender pink flowers,
3. a compact clumping habit,
4. and excellent vigor.

The new variety has been reproduced only by asexual propagation (cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old Tradescantia 'Sunshine Charm' growing in the field in late spring in Canby, Oreg.

DETAILED PLANT DESCRIPTION

The following is a detailed description of the new *Tradescantia* cultivar based on observations of a two-year-old specimen grown outside in full sun in the trial beds in the field in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Upright.

*Type.*—Herbaceous perennial.

*Cold hardiness.*—USDA Zone 4-9.

*Size.*—Grows to 55 cm wide and 45 cm tall to the top of the foliage and flowers.

*Vigor.*—Excellent.

*Stem.*—Oval in cross section, swollen at nodes and leafy, grow to 12 mm wide and 45 cm tall, glabrous, internodes range from 8 to 18 cm long, Yellow Green 144A.

*Roots.*—Thick and fleshy, plants root easily from nodes or crown division.

Leaf:

*Type.*—Simple.

*Arrangement.*—Alternate.

*Shape.*—Linear, sometimes folded closed from midvein.

*Venation.*—Parallel.

*Leaf description.*—Grows to 32 cm long and 35 mm wide, entire, glabrous inside and out except near base where villous on margin, entire, tip acuminate, base perfoliate.

*Leaf color.*—Varies with light, top and bottom side, ranges from Yellow 13B near the tip to Yellow Green 144A at the base.

Inflorescence:

*Type.*—Terminal umbel-like cyme subtended by 1 or 2 leafy bracts (smaller than the leaves, otherwise the similar, grow to 22 cm long, 32 mm wide, linear to linear lanceolate, top and bottom side Yellow 13B to Yellow Green 144A).

*Number of flowers per cyme.*—Up to 40.

*Size of inflorescence.*—4 cm tall and 4 cm wide.

*Peduncle.*—None.

*Pedicel.*—20 mm long and 1.2 mm wide, glabrous, flattened, Purple 77A to Red Purple 61A.

*Bloom period.*—Late May through July in Canby, Oreg.

Flower bud:

*Size.*—12 mm long and 7 mm wide at the widest point prior to opening.

*Description.*—Ovoid.

*Surface texture.*—Pubescent.

*Color.*—Yellow Green 145A mostly with top ¼ Yellow Green 148B and sometimes visible between closed sepals, Purple 77A.

Flower:

*Type.*—Actinomorphic to irregular, single or semi double.

*Size.*—43 mm wide and 10 to 15 mm deep.

*Corolla description.*—3 to 6 petals, each broadly ovate to orbicular in shape, sometimes somewhat pleated at the midrib, 17 mm wide and 20 mm long, entire, obtuse, attenuate, glabrous on both sides, top side Purple Violet 82A, bottom side Purple Violet 82B.

*Calyx description.*—3 to 4 sepals, can grow to 12 mm long and 7 mm wide, pubescent outside and glabrous inside, ovate, cupped, entire, acute, Yellow Green 144A on bottom ⅔ and Greyed Purple 185B on top ⅓ inside and out.

*Pistil description.*—1 in number, 10 mm long, ovary 2 mm long, Yellow Green 145C, style 8 mm long, Purple Violet 82A; stigma Yellow White 158A.

*Stamen description.*—6 in number, 8 mm long, filaments 7 mm long, Purple Violet 82A with long Purple Violet 82A hairs on bottom ⅔, anthers reniform in shape, 0.5 mm long, Yellow 11A, pollen abundant, Yellow 12A.

*Fragrance.*—None.

*Lastingness.*—A cyme blooms for about 4 weeks on the plant.

Fruit/seed: Fruit a 3-valved, 3-loculed capsule, 1 seed found for 50 flowers, extremely low fertility, seeds oval, 5 mm long and 3 mm wide, Black 202A.

Pests and diseases: *Tradescantia* Andersoniana Group are known to be susceptible viruses, aphids, and spider mites. The new cultivar has no known resistances but has shown no problems in Canby, Oreg.

I claim:

1. A new and distinct cultivar of *Tradescantia* plant substantially as shown and described.

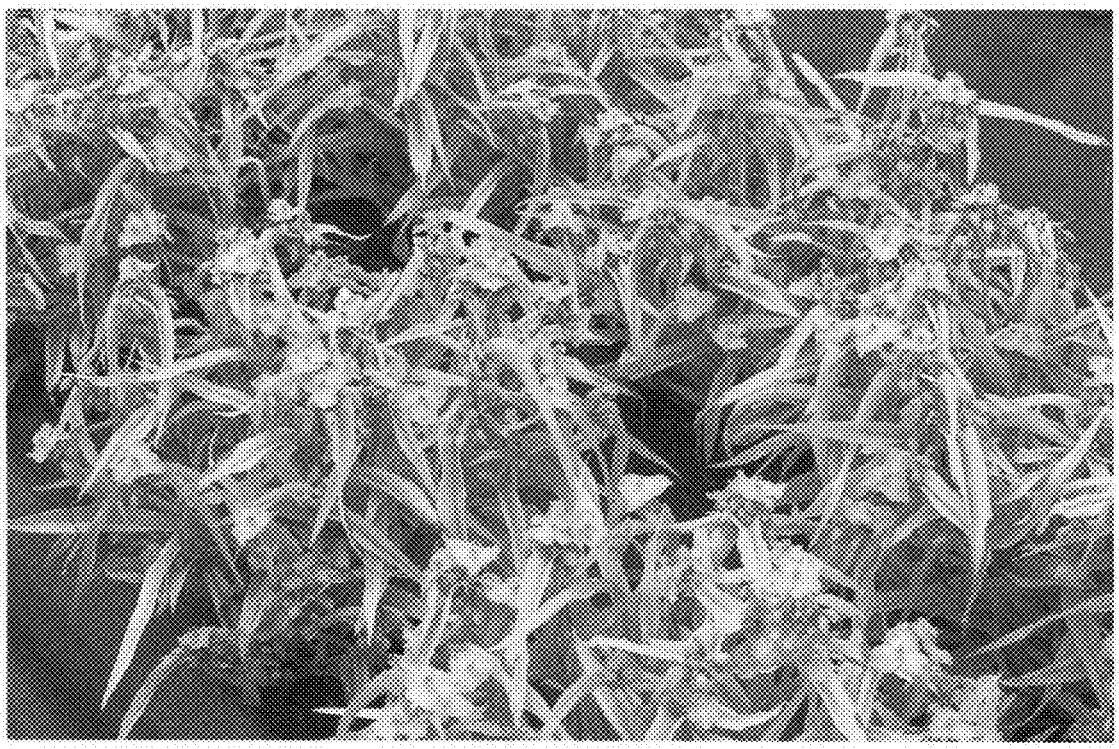

* * * * *